(12) United States Patent
Canning

(10) Patent No.: US 6,766,078 B1
(45) Date of Patent: Jul. 20, 2004

(54) GRATING STRUCTURE AND OPTICAL DEVICES

(75) Inventor: John Canning, Carlton (AU)

(73) Assignee: The University of Sydney (AU)

( * ) Notice: Subject to any disclaimer, the term of this patent is extended or adjusted under 35 U.S.C. 154(b) by 55 days.

(21) Appl. No.: 10/031,199
(22) PCT Filed: Jul. 10, 2000
(86) PCT No.: PCT/AU00/00827
§ 371 (c)(1), (2), (4) Date: Jun. 27, 2002
(87) PCT Pub. No.: WO01/06279
PCT Pub. Date: Jan. 25, 2001

(30) Foreign Application Priority Data

Jul. 15, 1999 (AU) .............................................. PQ1655

(51) Int. Cl.[7] .......................... G02B 6/26; G02B 6/42; G02B 6/16; G02B 6/02
(52) U.S. Cl. ........................... 385/37; 385/31; 385/123
(58) Field of Search ........................... 385/37, 123, 31, 385/137

(56) References Cited

U.S. PATENT DOCUMENTS

| 4,807,950 | A | * | 2/1989 | Glenn et al. ................. 385/123 |
| 5,140,149 | A | | 8/1992 | Sakata et al. |
| 5,164,956 | A | | 11/1992 | Lang |
| 5,367,588 | A | | 11/1994 | Hill et al. |
| 5,631,762 | A | | 5/1997 | Kataoka |
| 5,768,454 | A | | 6/1998 | Chesnoy et al. |
| 5,945,261 | A | * | 8/1999 | Rourke ........................ 430/321 |
| 6,072,926 | A | * | 6/2000 | Cole et al. ..................... 385/37 |
| 6,201,918 | B1 | * | 3/2001 | Berkey et al. ............... 385/128 |
| 6,381,052 | B1 | * | 4/2002 | Delisle et al. ................ 398/87 |

FOREIGN PATENT DOCUMENTS

| EP | 386797 | 9/1990 |
| GB | 2 209 408 | 5/1989 |
| WO | WO 86/01286 | 2/1986 |

OTHER PUBLICATIONS

Optics Communications, vol. 171, Dec. 1999 (Elsevier), J. Canning, M.G. Sceats, and S. Fleming, "Granting structures with phase mask period in silicon–on–silicon planar waveguides", pp. 213–217.

Derwent Abstract Accession No. 95–015352/02, DE 44190308 A (Hitachi Kiki KK) Dec. 8, 1994—Abstract— See U.S. Equivalent 5,631,762.

* cited by examiner

*Primary Examiner*—Brian Healy
*Assistant Examiner*—Tina M Lin
(74) *Attorney, Agent, or Firm*—Stites & Harbison PLLC, Marvin Petry

(57) ABSTRACT

An optical waveguide (1) has a grating structure (2) in which gratings of different orders are superimposed. When first and second order gratings are superimposed, input light is partially reflected by the first order component and partially coupled out of the waveguide by the second order component. The second order component can also be used to couple external light into the waveguide (1). The grating structure (2) has applications to free space couplers, optical sensors, and suppression of ripples in dispersion compensators.

20 Claims, 10 Drawing Sheets

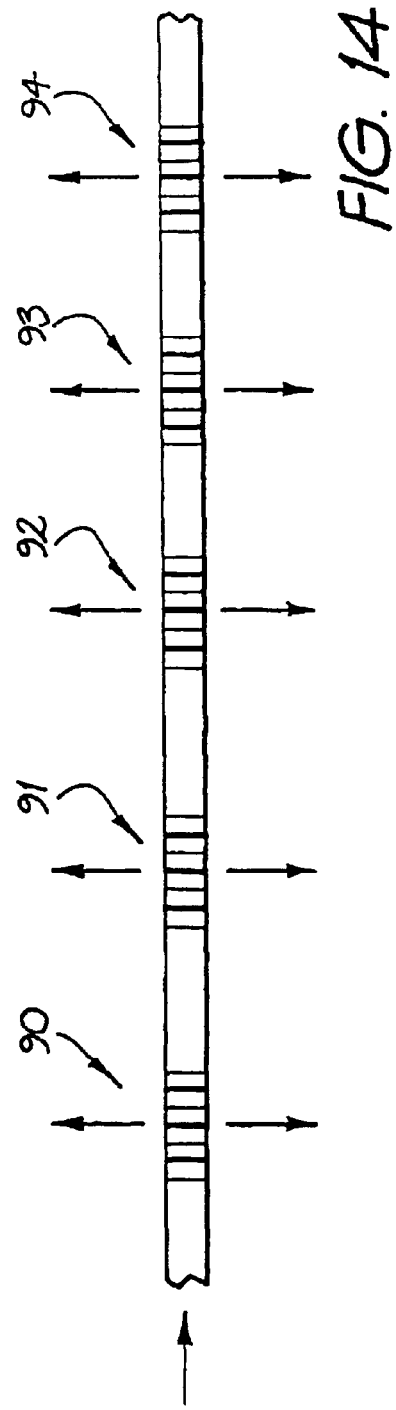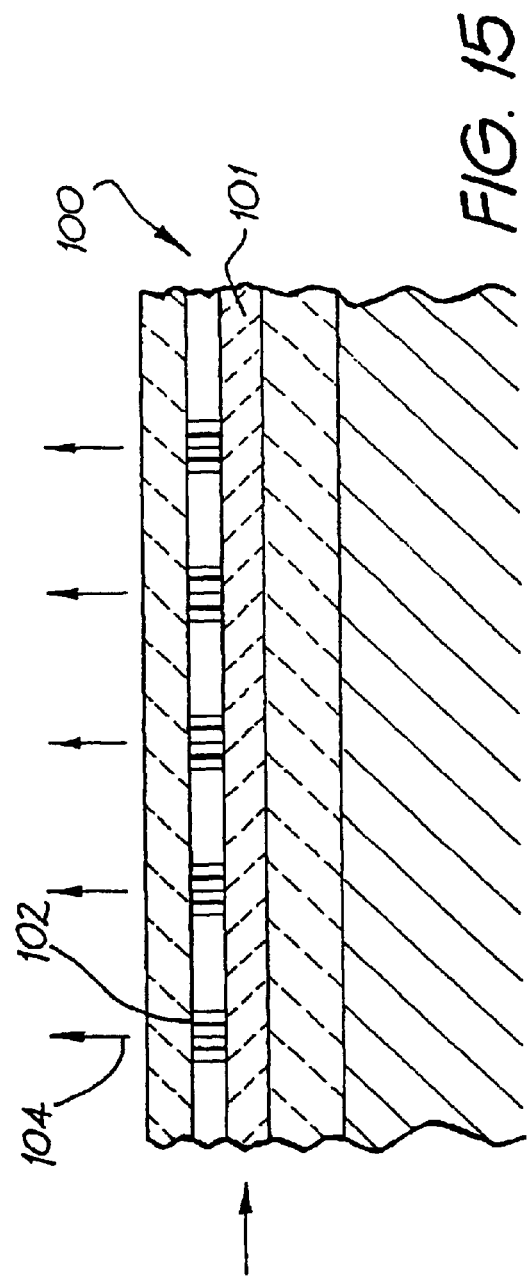

GRATING STRUCTURE AND OPTICAL DEVICES

FIELD OF THE INVENTION

The present invention relates broadly to a novel grating structure and to devices incorporating such grating structures.

BACKGROUND OF THE INVENTION

Optical devices have become increasingly important in the telecommunications field in general. In particular the transmission of data by optical fibers is an attractive alternative to conventional data transmission systems.

Accordingly, there is a great interest in development of optical devices which facilitate e.g. data transfer by optical fibers. Many optical device designs incorporate grating structures for various optical processing functions, including for example for filtering or sensing.

To facilitate the design of new optical devices, it is therefore desirable to provide new grating structures which may allow new functionality in optical devices.

SUMMARY OF INVENTION

In accordance with a first aspect of the present invention there is provided a grating structure in an optical waveguide, the grating structure being composed of a material having a refractive index variation and the grating structure comprising different order gratings superimposed.

In the context of the present invention the expression "different order" is to be understood as meaning different order with respect to a common wavelength.

A higher order, superimposed grating can result, in use, in the emission of filtered light energy out of the waveguide. This can be utilised e.g. for coupling between waveguides or for introducing a loss mechanism.

In one embodiment, the grating structure may comprise a first and a second order gratings superimposed.

At least one of the different order gratings may be chirped.

At least one of the different order gratings may be sampled.

At least one of the different order gratings may be apodised.

In accordance with another aspect of the present invention, there is provided an optical filter in an optical waveguide, the filter comprising the grating structure of the present invention.

The filter may comprise a chirped second order grating superimposed on a first order grating, the second order grating transmitting, in use, predetermined wavelengths of light energy substantially perpendicular to a core axis of the waveguide and at predetermined positions along the waveguide.

In one application, the filter can be utilized in a spectrographic device. In another application, the waveguide can comprise a distributed feed back laser or distributed Bragg reflectance laser and the filtered light energy forms the emission from the laser. In a further application, the second order grating structure can comprise a series of separate spaced apart second order gratings. In a further application, the grating structure can be formed with a spatially varying amount of zero order modulation along its length.

In accordance with another aspect of the present invention, there is provided an optical free space coupler in an optical waveguide, the coupler comprising a first grating structure in accordance with the present invention.

Preferably, the first grating structure is formed within a first optical waveguide and is arranged to provide the emission of filtered light energy substantially perpendicular to a core axis of the first waveguide; and a second grating structure formed within a second optical waveguide placed in the path of emission of the filtered light energy can couple a portion of the filtered light energy along the second optical waveguide.

At least one of the first or second grating structures may comprise a first order grating and a second order grating superimposed.

The coupler can be used as a sensor when a sample volume is used through which the filtered light energy passes before coupling with the second second order grating. Portions of the first waveguide or the second waveguide are preferably coated with a reflective material which concentrates the filtered light energy along a predetermined path of transmission from the first second order grating to the second second order grating.

In accordance with another aspect of the present invention there is provided an optical sensor in an optical waveguide, the sensor comprising the grating structure of the present invention.

The grating structure preferably comprises a second order grating superimposed on a first order grating formed within an optical waveguide, the grating structure having a predetermined second order modulation so as to provide for the reciprocal emission of optical energy substantially perpendicular to the optical waveguide; the sensor further comprising an optically sensitive material spaced adjacent to the optical waveguide, the material having optical reflective properties variable in accordance with an external physical parameter, the material reflecting the emitted optical energy from the grating structure back to the grating structure.

In accordance with another aspect of the present invention there is provided a device for suppressing ripples in a dispersion compensator in an optical fibre, the device comprising the grating structure of the present invention for providing an optical loss mechanism to effect the suppressing of the ripples.

Preferably, the grating structure comprises a second order grating superimposed on a first order grating.

In accordance with another aspect of the present invention there is provided a dispersion compensator for compensating dispersion in an optical fibre, the compensator comprising the grating structure of the present invention for providing an optical loss mechanism for suppressing ripples.

The grating structure may comprise a second order grating superimposed on a first order grating.

In the aforementioned arrangements, the grating structure can be formed offset from a central axis of the optical waveguide so as to provide directional perpendicular emission. Furthermore, it will be appreciated by a person skilled in the art that other higher order grating structures (i.e. higher than second order) may be utilised. In the description of preferred embodiments given below, calculations are presented for second order gratings (and gratings formed from first order and second order gratings superimposed). It will be appreciated that similar calculations can be performed for higher order gratings, however, it is noted that the loss characteristics will vary between different higher order gratings. E.g. the angular directionality of the loss will differ.

BRIEF DESCRIPTION OF THE DRAWINGS

Notwithstanding any other forms which may fall within the scope of the present invention, preferred forms of the invention will now be described, by way of example only, with reference to the accompanying drawings in which:

FIG. 14 illustrates a second order grating application to distribute emissions;

FIG. 15 illustrates the process of writing a second order grating on one side of a waveguide;

DESCRIPTION OF THE PREFERRED AND OTHER EMBODIMENTS

In the preferred embodiment, a grating structure is created which allows for the emission of optical energy substantially perpendicular to the grating structure. This is provided through the utilisation of high order coupling to radiation modes out of the gratings.

Figure 1:
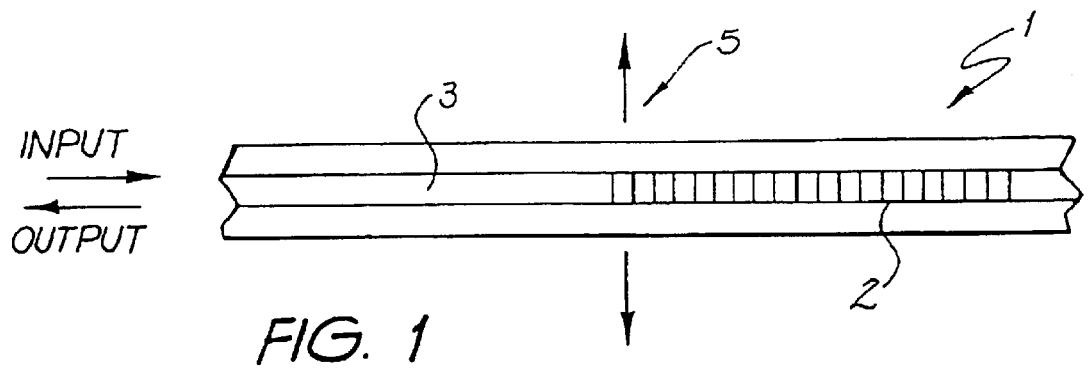
FIG. 1 is a schematic illustration of the operation of a second order grating.

Turning initially to FIG. 1, there is illustrated an optical fibre 1 having a grating structure 2 with light being transmitted along the core 3 of the fibre and the grating 2 reflecting a portion of the light in addition to transmitting a portion 5 in a perpendicular direction.

A guided light wave travelling along the fibre 3 with a propagation constant $\beta_g$ will interact with the Fourier components of the grating 2 to excite radiation modes with propagation constant $\beta_r \approx \text{Re}(\beta_g) - 2\pi p/\Lambda$ (p=±1,±2, . . . ) where $\Lambda$ is the grating period. Radiation modes with propagation constant $\beta_r$ only exist if $|\beta_r| < 2\pi n_2/\lambda$, where $\lambda$ is the free space wavelength and $n_2$ is the cladding index of the fibre 1. Therefore, in a first-order grating with $\text{Re}(\beta_g) \approx \pi/\Lambda$ and $2\pi n_2/\lambda < \text{Re}(\beta_g) < 2\pi n_1/\lambda$, no radiation modes can be excited. However, for blazed gratings and higher order gratings this is no longer the case. Blaze is readily removed with accurate alignment in most writing setups and is therefore not a major consideration. On the other hand, for a second order grating, $\text{Re}(\beta_g) \approx 2\pi/\Lambda$. This means that for p=±1 the guided mode propagating both backwards and forwards in the grating will couple with radiation modes for which $\beta_r \approx 0$. For a radiation mode with propagation constant $\beta_r$, the radiation angle in the cladding layer is given by:

$$\theta = \arccos\left[\frac{\beta_r}{(2\pi n_2/\lambda)}\right] \quad \text{(Eq. 1)}$$

The radiation angle in the second order grating is therefore 90° and first-order radiation loss will occur. Strong directionality is expected. The amount of loss will be dependent on a number of factors including index modulation, index modulation profile and penetration of UV-induced index change across the waveguide core which determines the intensity profile of radiation loss around the waveguide—analogous to the behaviour predicted with different tooth-shaped index profiles in semiconductor radiation-coupled gratings and also previously experimentally observed in fibre gratings. The presence of a 2nd order grating therefore can lead to significant light coupled out of the side of a Bragg grating.

In one embodiment of the invention, second order gratings can be constructed through the utilisation of the zero order diffraction mode when writing the grating.

Figure 2:
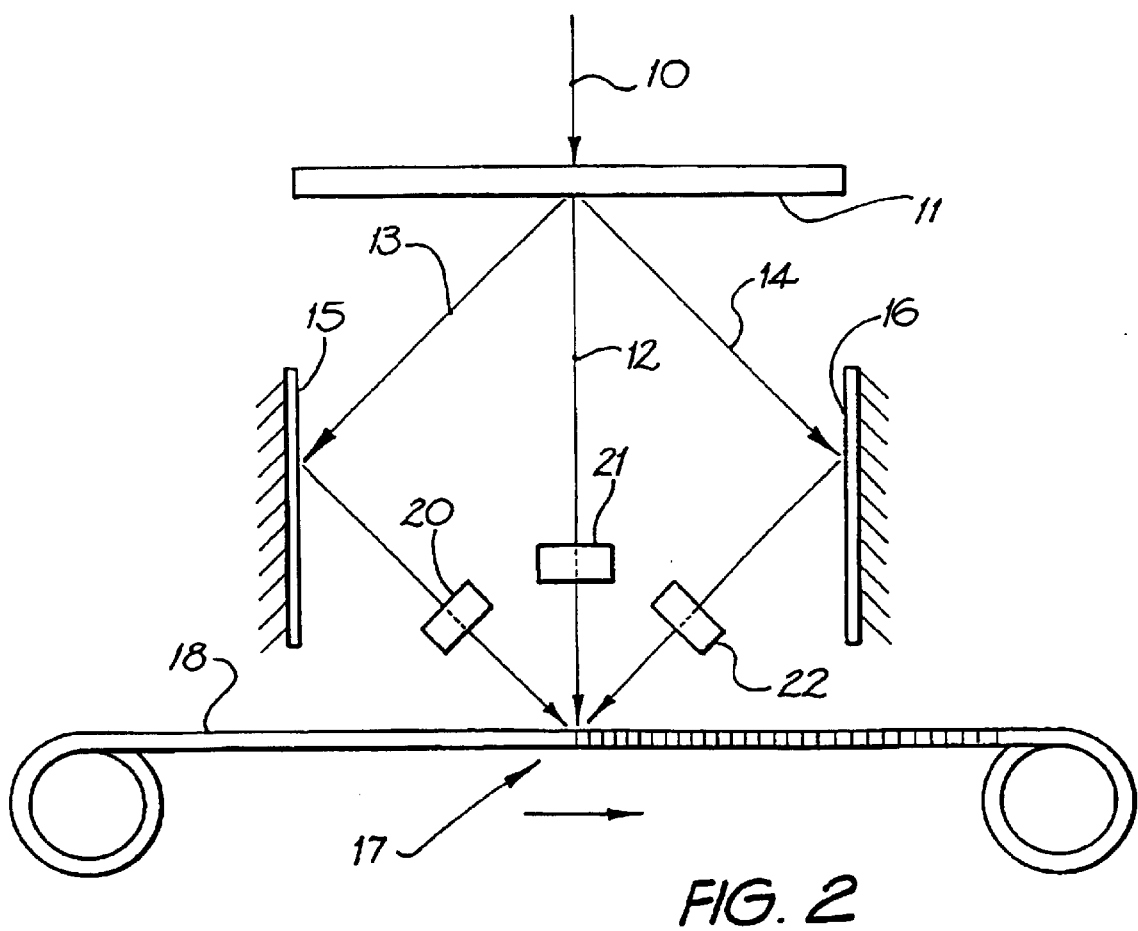
FIG. 2 illustrates a first grating writing system for writing second order gratings.

A number of different techniques for utilising the zero order are possible. In one embodiment, a three or more beam interference arrangement as schematically illustrated in FIG. 2 can be used. An initial coherent beam 10 is being projected through a phase mask 11 so that three beams including a zero order beam 12 and two first order beams 13, 14 are output. The two beams 13, 14 are reflected by a mirror 15, 16 so as to interfere at point 17 so as to produce an interference pattern. A photosensitive fibre 18 is placed at this point such that the interference pattern is imprinted in the fibre, normally by way of reflective index variation in accordance with the interference pattern. In the preferred embodiment, the zero order beam 12 is also projected onto the fibre at the same point 17 so as to provide for a second order grating to form a hybrid grating comprising first and second order gratings. Preferably, an attenuator 21 and phase modulation or attenuation elements 20, 22 are provided so as to control the amount of the zero order relative to the first order in addition to controlling the phase of the pattern formed on the optical fibre 18. In this manner, chirping and other effects can be produced in addition to a controlled mixing of the amount of the zero order beam.

Figure 3:
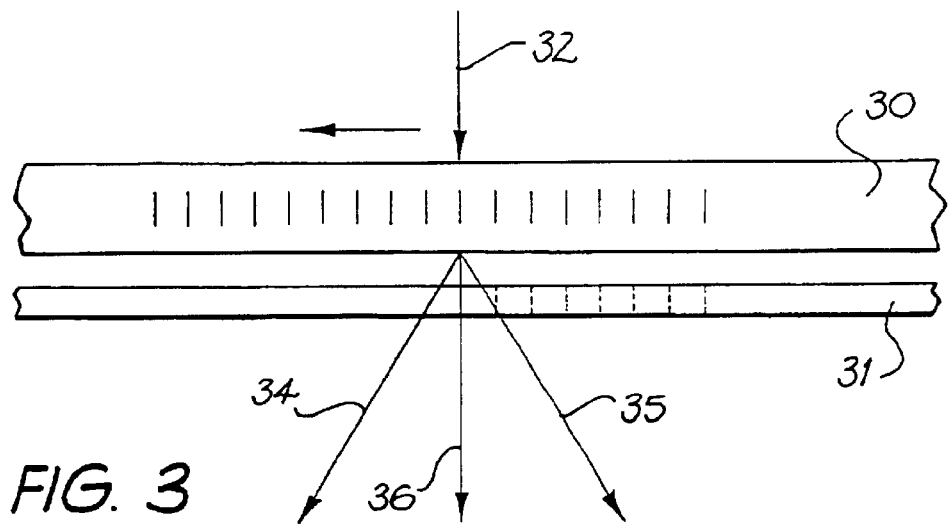
FIG. 3 illustrates a second possible grating writing system for writing second order gratings.

Other arrangements are possible which control the amount of zero order beam. For example, in FIG. 3, there is illustrated schematically a "direct writing" system wherein a phase mask 30 is provided and a fibre 31 is placed behind the phase mask. A coherent UV beam 32 is swept along the phase mask which produces a first order interfering beam 34, 35 in addition to a zero order beam 36. In the arrangement of FIG. 3 varying the depth of the phase mask 30 can be used to alter the amount of zero order beam.

Hence, in the preferred embodiments, a super structure grating of both first and second order periodicities is formed utilising the zero order and first order beams.

The basic premise in the mechanism arises from significant zero order interaction with the +1 and −1 diffraction orders of a phase mask. The angle of each diffracted beam, $\theta_m$, can be calculated from the expression for monochromatic light incident on a diffraction grating:

$$\sin\theta_n = \sin\theta_i + m\frac{\lambda}{\Lambda} \quad \text{(Eq. 2)}$$

where $\theta_i$ is the angle of the incident beam (0° when normal to the diffraction grating), m is the diffraction order, $\lambda$ is the writing wavelength, and $\Lambda$ is the phase mask period. Using the appropriate angles, the period is $\Lambda_{m,n}=\lambda/\sin(\theta_{m,n})$, where $\theta_{m,n}$ is the angle between the two orders. This expression is similarly derived to that in equation (1). To determine this amplitude the intensity can be calculated by squaring the sum of the real and complex components of the individual amplitudes, $a_N$, where N is the diffraction order of the phase mask:

$$I=|a_0\exp(jkx\sin\theta_0)+a_1\exp(jkx\sin\theta_1)+a_{-1}\exp(jkx\sin\theta_{-1})|^2 \quad \text{(Eq. 3)}$$

The angular quantity, $\theta_N$, which determines the phase of each wave, is obtained from $$\theta_n = \sin^{-1}\left(\frac{N\lambda}{nd}\right) \quad \text{(Eq. 4)}$$

where d is the phase mask period (specified in experiments as 1.064 $\mu$m). The above formulation calculates the electric field distribution immediately after the phase mask. This is suitable for direct contact printing of gratings on rib waveguides but in most instances an additional term in the amplitude of each wave is required for buried waveguides and optical fibres where the core is at a distance from the phase mask determined by a cladding. Talbot planes away from the phase mask surface, which can have a period with dimensions less than the waveguide, are neglected.

Figure 4:
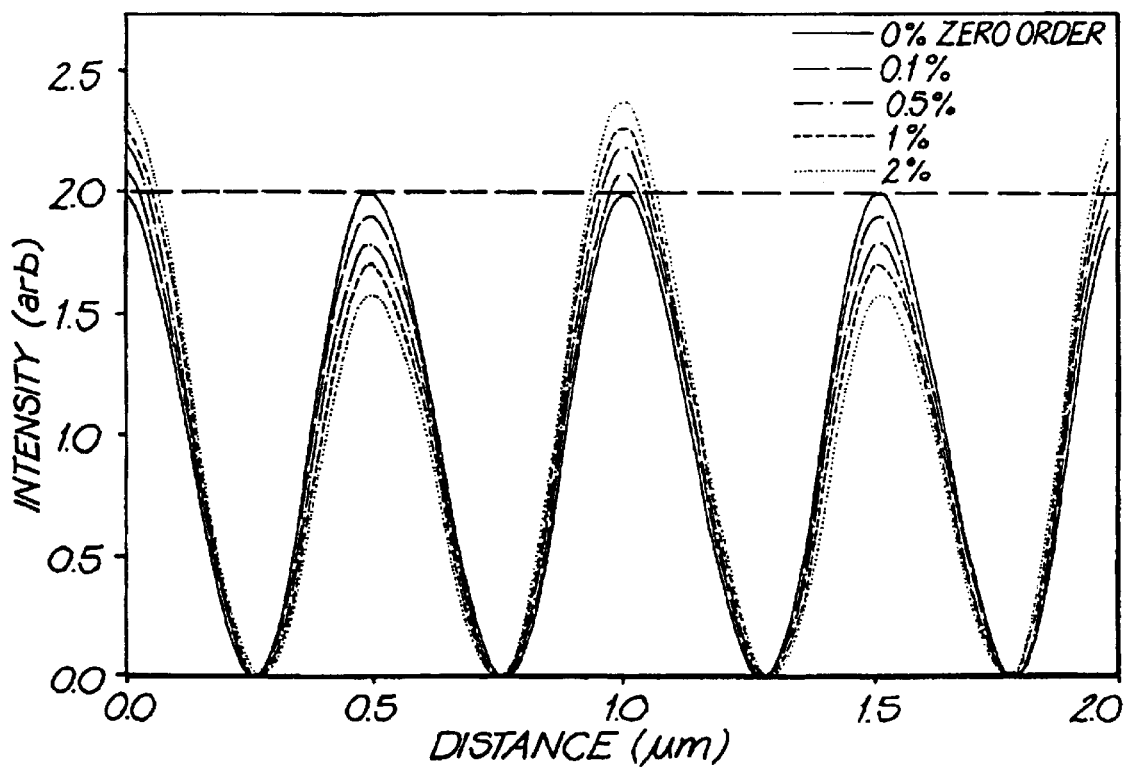
FIG. 4 is an intensity graph having different zero orders.
Figure 5:
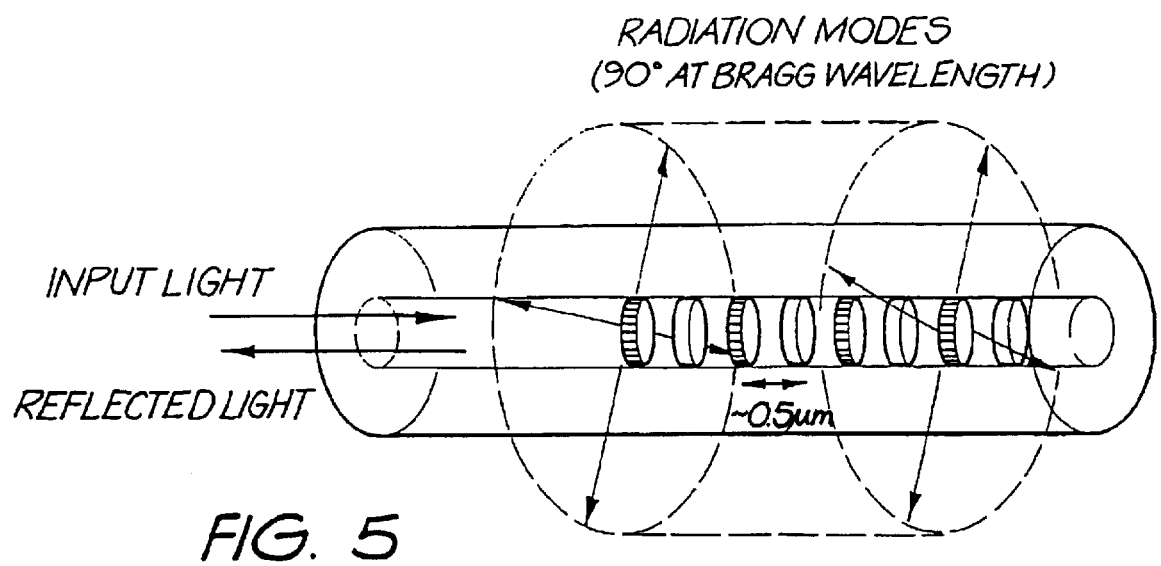
FIG. 5 illustrates the perpendicular radiation modes for a second order grating.

FIG. 4 shows the calculated intensity distribution arising from the interactions between the 0, +1, and −1 orders for varying amounts of zero order. Assuming most of the incoming light is in these orders the intensity at the peaks of the interference between these orders will always be substantially larger than the intensity of the incoming light. Notably, even when the zero order is only 1% of the input light a substantial peak intensity maximum occurs every 1 $\mu$m. Since the phenomenological growth of index with UV is often not linear, this disparity can be much larger when examining the generated index profile. FIG. 5 is a schematic of such a small complex grating with a small amount diffracted light coupling to radiation modes with $\beta_r=0$.

As a consequence of this superposition of the interference between the zero order and the +1 and −1 orders, there exists a component of a 2nd order grating. Diffraction at the Bragg wavelength of the first order grating occurs at ninety degrees at those wavelengths satisfying the criterion of twice the pitch of the Bragg grating; i.e. $\Lambda_{2nd}=\Lambda_B/N=2\Lambda_B$. The relative intensity depends on the ratio of the peak index amplitude of the 2nd order grating with that of the Bragg grating: $\Delta n_{2nd}/\Delta n_B$. To quantify the expected losses systematic and careful measurements of a number of parameters, including grating growth curves and the intensities of diffracted phase mask orders, is required. However, the losses in these complex combination gratings superstructures will always be less than that of a strong pure second order grating that can couple up to 3 dB of its light to radiation modes orthogonal to the grating axis.

The second ordered grating structure can therefore be utilised in a number of ways in different photonics devices through appropriate control of the zero order component of any beam. Various devices will be discussed herein after under separate headings.

Filters

Figure 6:
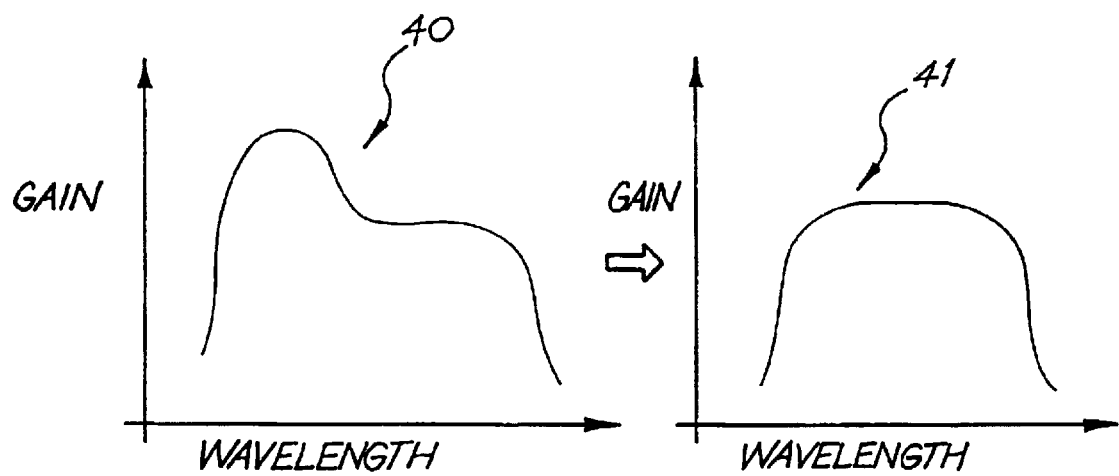
FIG. 6 illustrates a series of graphs showing amplifier gain manipulation through filtering.
Figure 7:
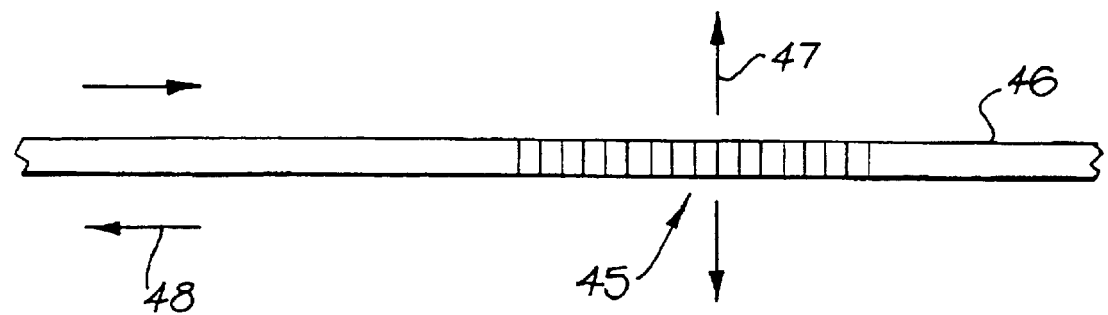
FIG. 7 is a schematic illustration of an example application of a second order grating.

Often, it is necessary to provide for filtering of optical signals. In one particularly common case is the gain flattening of, for example, Erbium doped fibres. The gain of an Erbium doped fibre tends to vary with wavelength and is shown schematically 40 in FIG. 6. It is obviously desirable to provide for the same level of gain across a wide bandwidth. It is also desirable to provide a variable filter such that the gain is substantially constant 41 across a wavelength. Such a filter can be constructed as illustrated in FIG. 7 wherein a second order grating 45 is formed in a fibre 46. The grating 45 can be a chirped grating having predetermined reflectance criteria at different frequencies. The grating is also modulated by a zeroth order beam so as to radiate e.g. 47 variable mounts of light with the degree of radiation of the beam being higher when high levels of gain are present at the particular wavelength. In this manner, a superstructure of first and second order gratings can be written so as to radiate energy and therefore provide for gain flattening. The resulting output 48 is a gain flattened narrow band response. The arrangement of FIG. 7 can also be configured to operate in a transmission mode. Advantageously, it has low sensitivity to cladding mode variations.

Spectrometers

Figure 8:
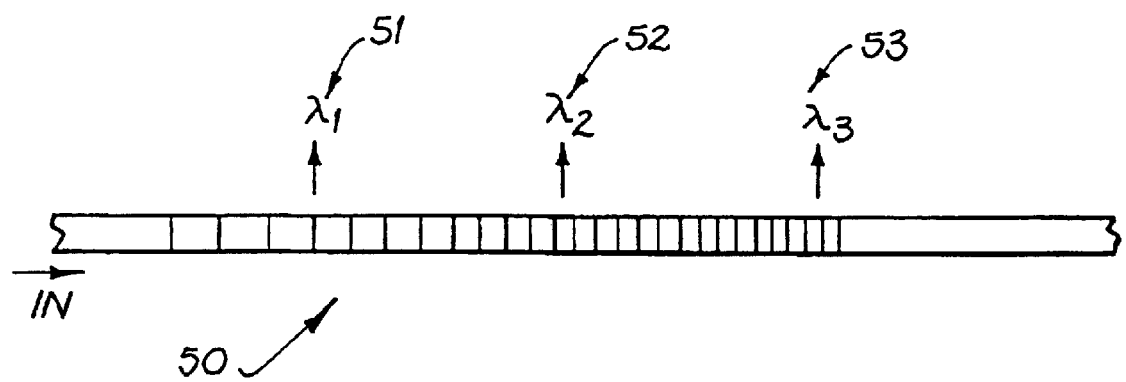
FIG. 8 is another example illustration of an application of a second order grating.
Figure 9:
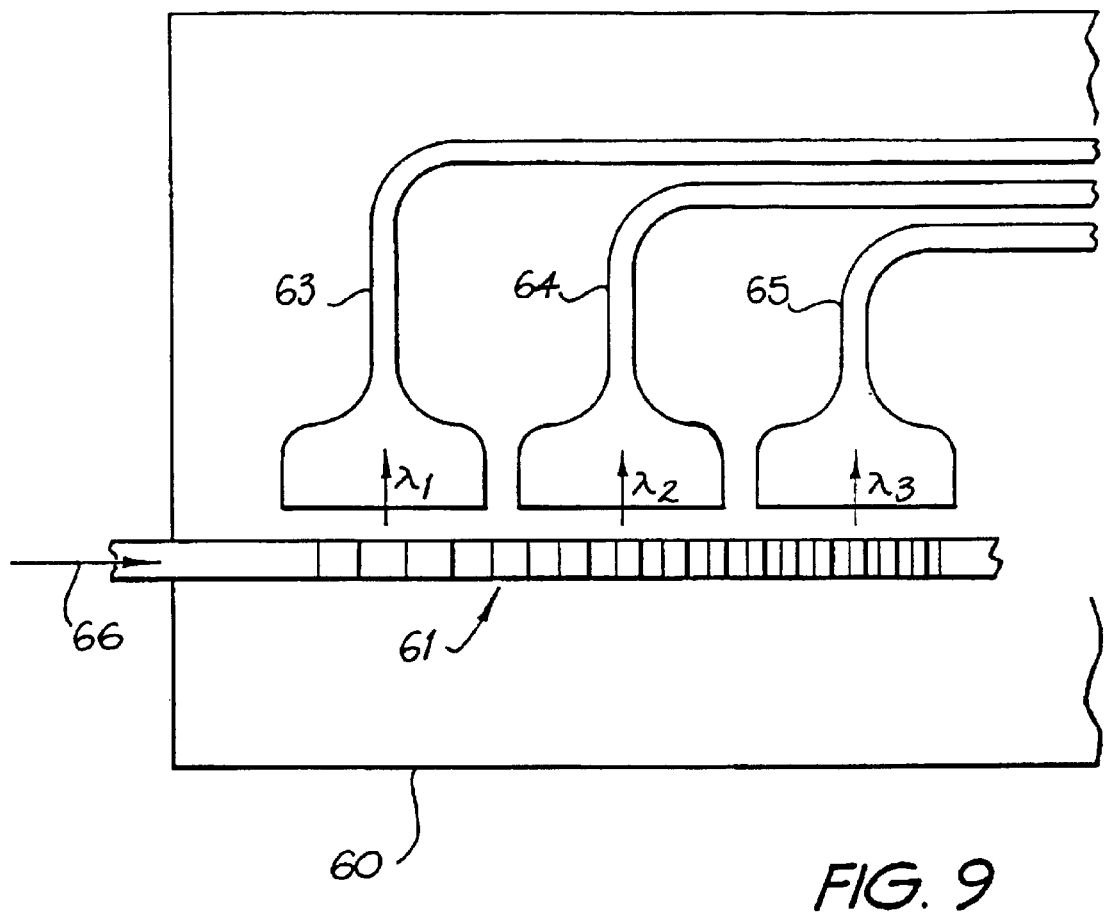
FIG. 9 illustrates a further application of a chirped second order grating.

The principle of FIG. 7 can be extended to the construction of a spectrometer type device. Such an arrangement is illustrated in FIG. 8 wherein a chirped grating 50 is provided having both first and second order grating structures. Hence, different wavelengths e.g. 51, 52, 53 will be emitted in a perpendicular direction depending on the periodicity of the chirp. The arrangement of FIG. 8 can hence be utilised in spectrometric analysis or in wavelength division multiplexing filters. The arrangement of FIG. 8 can be extended to a planar waveguide form as illustrated in FIG. 9 wherein a wave guide 60 contains a chirped grating structure 61 which emits wavelengths $\lambda_1$, $\lambda_2$, $\lambda_3$,. Three collectors 63–65 are provided for collecting the emitted light which can be forwarded for analysis. Hence, the input light 66 will be divided into its wavelength channels.

Surface Emitting Gratings

Figure 10:
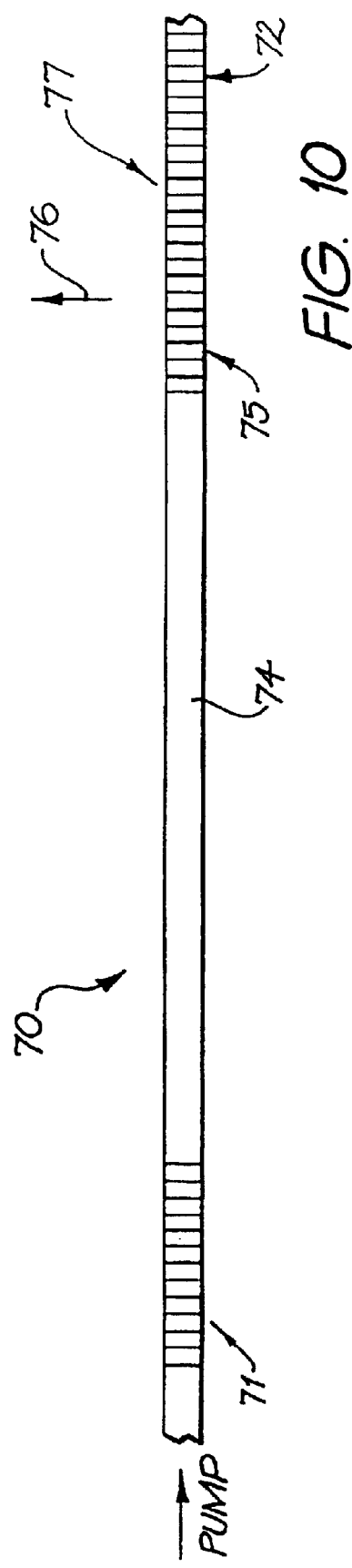
FIGS. 10 and 11 illustrate a laser application of a second order grating.

The construction of superimposed grating structures can be extended to the formation of surface emitting grating structure for use in lasers etc. An initial example of an arrangement is as illustrated in FIG. 10 wherein a laser structure 70 is provided with distributed Bragg reflectors 71, 72. A pump input causes the intermediate portion 74 to laze and a second order grating 75 of the superimposed grating structure 77 is provided for the emission 76 of the laser light, whilst the first order grating 72 of the superimposed grating structure 77 reflects.

Figure 11:
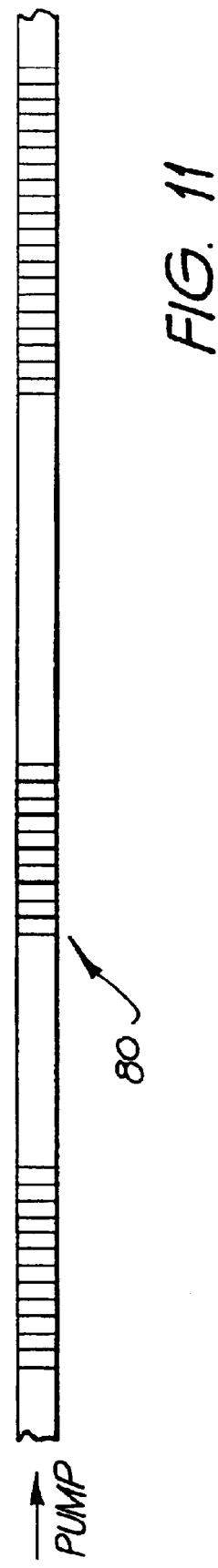

FIG. 11 illustrates an alternative arrangement wherein a separate superimposed grating structure 80 is provided for laser emission. The arrangement of FIGS. 10 and 11 can be extended to a distributed feedback (DFB) laser with the second order grating providing an interruption of the degeneracy of side mode. This allows for a large area pump lasers for integrated optics with easy coupling and high powers.

Figure 12:
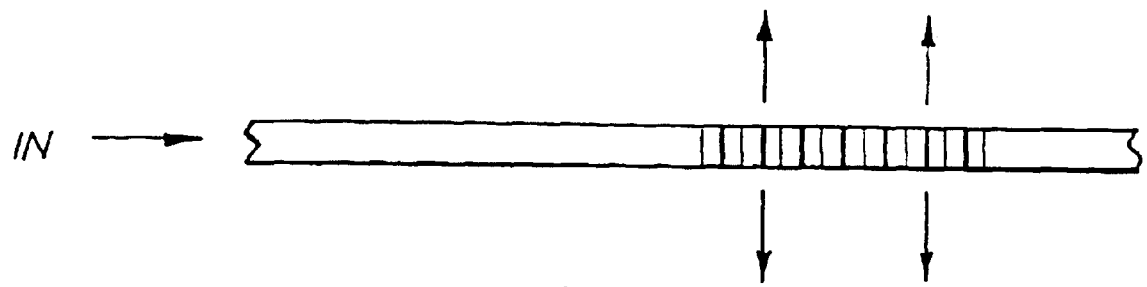
FIG. 12 illustrates a further application of a second order grating.

The superimposed grating structure can be utilised as illustrated in FIG. 12, as enlarged area "semi-coherent" emitter for utilisation as a sensor source etc.

Free Space Couplers

Figure 13:
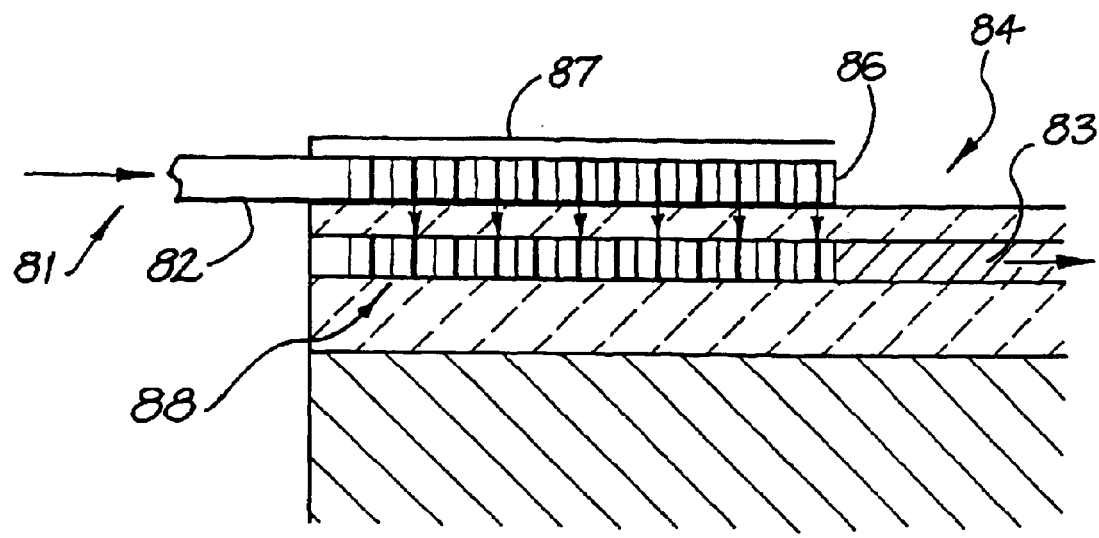
FIG. 13 illustrates the utilisation of second order gratings for waveguide coupling.

The utilisation of second order gratings can be extended to providing for free space coupling. A suitable arrangement as illustrated in FIG. 13 where it is desired to couple input light 81 transmitted along fibre 82 to a planar waveguide structure 84 having internal waveguide 83. A second order grating 86 is constructed in one end of the fibre 82 which also contains a reflective coating 87. The reflective coating reflects the light outputted perpendicular to the fibre 82 down to the waveguide 83 wherein a further second order grating 88 is formed. The grating 88 couples with the emitted light via the principle of reciprocity into the waveguide where it is output 83.

Control of Beam Divergence for Filters, Lasers, etc.

The principle of superimposed grating structures can be extended as illustrated in FIG. 14 to provide for a larger effective aperture through the utilisation of multiple second order gratings e.g. 90–94. A larger aperture or extended grating structure means less divergence and a quasi coherent output is possible from incoherent sources.

Ideally, to provide enhanced directionality, the side of transmission perpendicular to the waveguide is controlled. This can be achieved by writing gratings on one side of the waveguide. Such an arrangement is illustrated in FIG. 15 where a waveguide structure is shown 100 where light is transmitted along the waveguide 101 and a series of second order gratings e.g. 102 are provided on a first side of the waveguide 101. This results in a transmission perpendicular to the waveguide structure. This allows for complex integrated optic structures to be produced on a planar waveguide.

Large Areas Sensor Heads

Figures 16, 17:
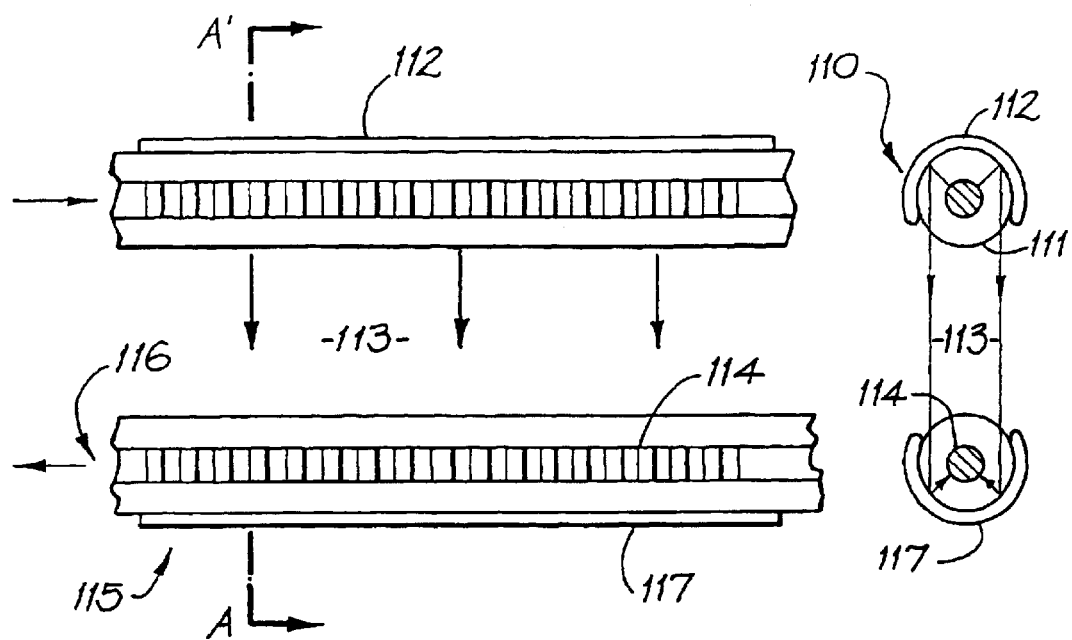
FIGS. 16 and 17 illustrate a sensing application of second order gratings.

The superimposed higher order grating principle can be extended to sensor heads with an example illustrated in FIGS. 16 and 17. A waveguide 110 is provided having a second order grating 111. Preferably, a reflective coating is formed around predetermined portions of the fibre 110 so as to reflect light downwards through a volume 113 which is to be sampled. A second fibre 115 is provided which couples the light travelling through the volume 113 to output 116. Again, a reflective coating 117 is also provided for enhanced coupled. FIG. 17 illustrates a sectional view through the line A–A' of FIG. 16 and more clearly illustrates the mirror portions 112, 117 which add to enhance the degree of coupling. The wavelength absorption in volume 113 will affect the spectra of output 116 which can be separately analysed to determine sensor operation.

Figures 18, 19:
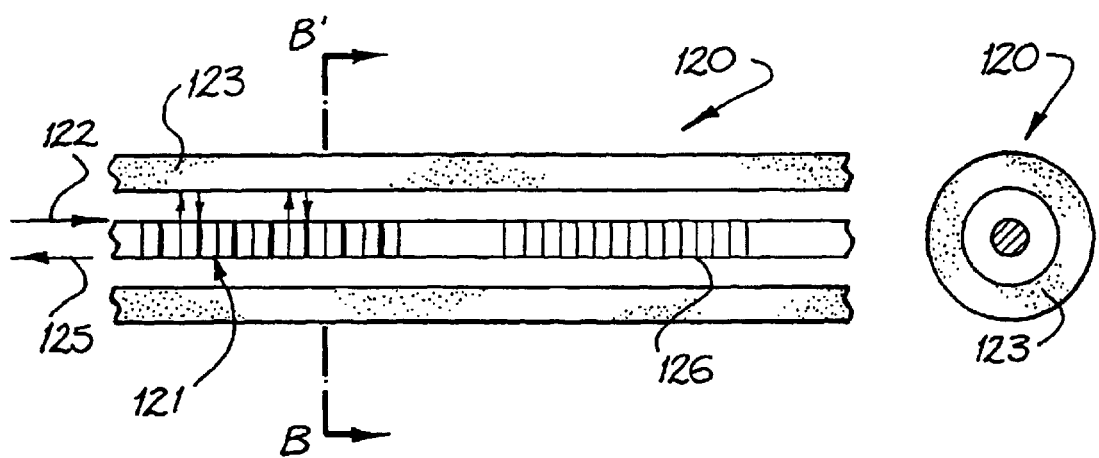
FIGS. 18 and 19 illustrate an alternative sensor application.

The arrangement of FIG. 16 and FIG. 17 can be extended as shown in FIG. 18 and FIG. 19 to the provision of wavelength specific sensors. FIG. 18 illustrates a side-view of a sensor arrangement with FIG. 19 illustrated in the corresponding sectional view taken through the line B–B' at FIG. 18. The arrangement 120 includes a second order grating 121 which transmits input light 122 in a perpendicular manner. A porous coating 123 is provided and is of a reflective type. Hence, the light reflected from the coating 123 is reflected back and coupled back by second order grating 122 where it is subsequently output 125. The reflective material 123 can be modulated to change the integrated reflection and the corresponding modulated output signal 125 returned. Alternatively, the reflective material may change properties with absorption of a species to be identified which allows for spectral analysis of the absorbed gas via variations in the output 125. A second gratings 126 is also provided for reflecting back light via the waveguide.

Narrow Band Attenuators

The superimposed higher order grating principle can be extended to provide a novel form of attenuator. Such an arrangement is illustrated in FIG. 20, wherein a chirped grating 130 is provided which includes a second order grating having controlled degrees of radiation loss to bounce an input signal 131 so as to provide bandwidth attenuation of output signal 132.

Tunable Narrow Bend Attenuator

Figure 20:
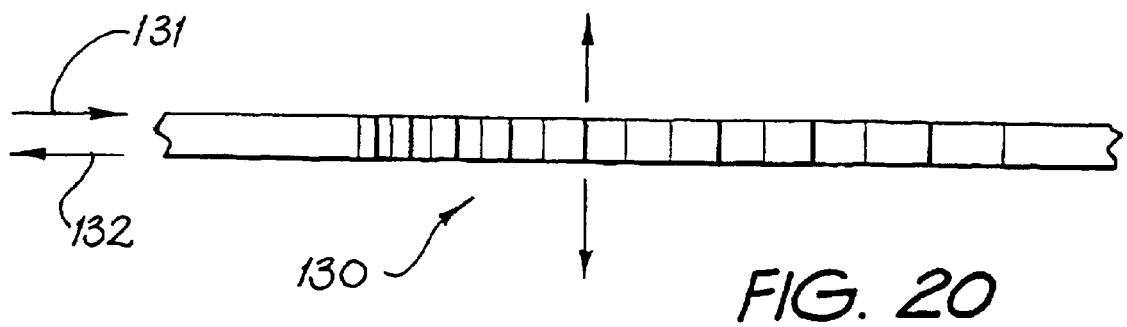
FIG. 20 illustrates a further application of second order gratings.
Figure 21:
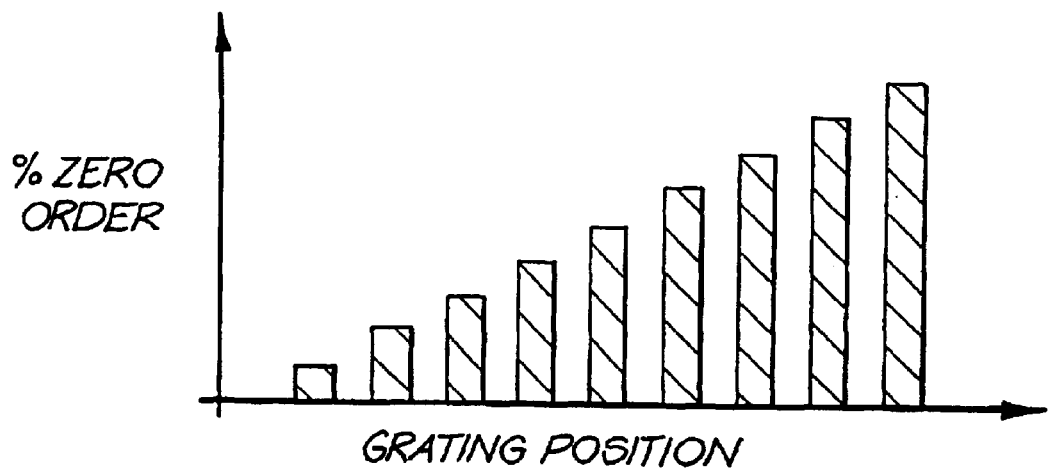
FIG. 21 illustrates the alteration of zero order component in a grating structure.

The arrangement in FIG. 20 can be extended by providing a chirped grating with a chirped index modulation provided by "chirping" the degree of zero order irradiation. The amount of zero order can be varied as illustrated in FIG. 21 with grating position. Such a chirped grating structure can then be subjected to stretching, pressure or heating. As the structure is stretched the narrow band position will move across a series of desired wavelengths. Further, stretching or compressing the grating structure will alter the amount of perpendicular radiation.

Dispersion Compensator

The principle of FIG. 20 can be extended to providing dispersion compensation wherein the grating structure 130 is written in an Erbium doped amplifying fibre or similar amplifier. The degree of radiation also can be controlled so as to provide for simultaneous dispersion compensation and radiation loss. By utilising a combination of first and second order grating structures, optimisation of the amount of loss can be achieved. The arrangement also allows for the suppression of cavity based ripples.

Photonic Band Gap and Generation

The arrangement of FIG. 2 also allows for the formation of complex Photonic band gap structures in the interference vicinity 17. The area of interference 17 will contain a complex interference pattern which can be imprinted on a photosensitive material. Such complex arrangements can be utilised to store information for later playback. By controlling the attenuators/phase elements 20–22 and/or the angles of the mirrors 15, 16 arbitrary complex structures can be formed. This interference regime is analogues to the complex interference formed where Talbot & Lohmann planes are generated within the Fresnel zone just after a phase mask grating.

It would be appreciated by a person skilled in the art that numerous variations and/or modifications may be made to the present invention as shown in the specific embodiments and devices without departing from the spirit or scope of the invention as broadly described. The present embodiments are, therefore, to be considered in all respects to be illustrative and not restrictive.

What is claimed is:

1. An optical waveguide having a grating structure, the grating structure being composed of a material having a refractive index variation, the grating structure comprising a first grating structure and a second grating structure of different, orders with respect to a certain wavelength superimposed, wherein:
   the first grating structure is arranged to provide, in use, the coupling of optical energy in a direction substantially perpendicular to a core axis of the waveguide; and
   the second grating structure is arranged to provide, in use, the coupling of optical energy in a direction substantially parallel to the core axis of the waveguide.

2. The grating structure as claimed in claim 1, wherein the grating structure comprises a first order grating and a second order grating superimposed.

3. The grating structure as claimed in claim 1, wherein at least one of the different order gratings is chirped.

4. The grating structure as claimed in claim 1, wherein at least one of the different order gratings is sampled.

5. The grating structure as claimed in claim 1, wherein at least one of the different order gratings is apodized.

6. An optical filter in an optical waveguide, the filter comprising the grating structure as claimed in claim 1.

7. An filter as claimed in claim 6, wherein the filter comprises a chirped second order grating superimposed on a first order grating, the second order grating transmitting, in use, predetermined wavelengths of light energy substantially perpendicular to a core axis of the waveguide and at predetermined positions along the waveguide.

8. An optical free space coupler in an optical waveguide, the coupler comprising a first grating structure as claimed in claim 1.

9. A coupler as claimed in claim 8, wherein the first grating structure is formed within a first optical waveguide and is arranged to provide the emission of filtered light energy substantially perpendicular to a core axis of the first waveguide; and a second grating structure formed within a second optical waveguide placed in the path of emission of the filtered light energy can couple a filtered light energy substantially perpendicular to a core axis of the first Waveguide; and a second grating structure formed within a second optical waveguide placed in the path of emission of the filtered light energy can couple a portion of the filtered light energy along the second optical waveguide.

10. A coupler as claimed in claim 9, wherein at least one of the first or second grating structures comprises a first order grating and a second order grating superimposed.

11. An optical sensor in an optical waveguide, the sensor comprising the grating structure as claimed in claim 1.

12. A sensor as claimed in claim 11, wherein the grating structure comprises a second order grating superimposed on a first order grating formed within an optical waveguide, the grating structure having a predetermined second order modulation so as to provide for the reciprocal emission of optical energy substantially perpendicular to the optical waveguide; the sensor further comprising an optically sensitive material spaced adjacent to the optical waveguide, the material having optical reflective properties variable in accordance with an external physical parameter, the material reflecting the emitted optical energy from the grating structure back to the grating structure.

13. A device for suppressing ripples in a dispersion compensator in an optical fiber, the device comprising the grating structure as claimed in claim 1 for providing an optical loss mechanism to effect the suppressing of the ripples.

14. A dispersion compensator for compensating dispersion in an optical fiber, the compensator comprising the grating structure as claimed in claim 1 for providing an optical loss mechanism for suppressing ripples.

15. An optical filter comprising an optical waveguide having a grating structure, the grating structure being composed of a material having a refractive index variation, the grating structure comprising a chirped second order grating superimposed on a first order grating, the orders of the gratings being defined with respect to a certain wavelength, wherein:
   the second order grating transmits, in use, predetermined wavelengths of light energy substantially perpendicular to a core axis of the waveguide and at predetermined positions along the waveguide; and
   the first order grating is arranged to provide, in use, the coupling of optical energy in a direction substantially parallel to the core axis of the waveguide.

16. A free space coupler comprising a first optical waveguide having a grating structure, the grating structure being composed of a material having a refractive index variation, the grating structure comprising a first grating structure and a second grating structure of different orders with respect to a certain wavelength superimposed, wherein:
   the first grating structure is arranged to provide, in use, the emission of filtered light energy in a direction substantially perpendicular to a core axis of the waveguide; and
   the second grating structure is arranged to provide, in use, the coupling of optical energy in a direction substantially parallel to the core axis of the waveguide, the free space coupler further comprising a second optical waveguide placed in the path of emission of the filtered light energy to couple a portion of the filtered light energy along the second optical waveguide.

17. An optical sensor comprising an optical waveguide having a grating structure, the grating structure being composed of a material having a refractive index variation, the grating structure comprising a second order grating superimposed on a first order grating and a second grating structure the orders of the gratings being defined with respect to a certain wavelength, wherein:

the second order grating has a predetermined second order modulation so as to provide, in use, for the reciprocal emission of optical energy substantially perpendicular to a core axis of the waveguide; and the first order grating is arranged to provide, in use, the coupling of optical energy in a direction substantially parallel to the core axis of the waveguide, the sensor further comprising an optically sensitive material spaced adjacent to the optical waveguide, the material having optical reflective properties variable in accordance with an external physical parameter, the material reflecting the emitted optical energy from the grating structure back to the grating structure.

18. A dispersion compensator for compensating dispersion in an optical fibre, the compensator comprising an optical waveguide having a grating structure, the grating structure being composed of a material having a refractive index variation, the grating structure comprising a first grating structure and a second grating structure of different orders with respect to a certain wavelength superimposed, wherein:

the first grating structure is arranged to provide, in use, the coupling of optical energy in a direction substantially perpendicular to a core axis of the waveguide for providing an optical loss mechanism for suppressing ripples; and the second grating structure is arranged to provide, in use, the coupling of optical energy in a direction substantially parallel to the core axis of the waveguide.

19. A method for coupling optical energy substantially perpendicular to a core axis of an optical waveguide, comprising the steps of:

providing a grating structure in the optical waveguide, the grating structure being composed of a material having a refractive index variation and comprising a first grating structure and a second grating structure of different orders with respect to a certain wavelength superimposed;

coupling optical energy, via the first grating structure, in a direction substantially perpendicular to a core axis of the waveguide; and coupling optical energy, via the second grating structure, in a direction substantially parallel to the core axis of the waveguide.

20. A method for providing dispersion compensation in an optical waveguide, comprising the steps of:

providing a grating structure in the optical waveguide, the grating structure being composed of a material having a refractive index variation and comprising a first grating structure and a second grating structure of different orders with respect to a certain wavelength superimposed;

providing an optical loss mechanism for suppressing ripples by coupling optical energy, via the first grating structure, in a direction substantially perpendicular to a core axis of the waveguide; and coupling optical energy, via the second grating structure, in a direction substantially parallel to the core axis of the waveguide.

* * * * *